US012594370B2

(12) United States Patent
Mei et al.

(10) Patent No.: US 12,594,370 B2
(45) Date of Patent: Apr. 7, 2026

(54) OPTIMIZING DEVICE FOR FREELY SWITCHING BETWEEN BLOOD CELL COMPONENT REMOVAL AND PLASMA EXCHANGE

(71) Applicant: XIANGYA HOSPITAL OF CENTRAL SOUTH UNIVERSITY, Changsha City (CN)

(72) Inventors: Cheng Mei, Changsha City (CN); Bijuan Li, Changsha City (CN); Yuanjun Jiang, Changsha City (CN); Wenyu Yin, Changsha City (CN); Xi Yuan, Changsha City (CN); Zhimin Zhang, Changsha City (CN); Linxi Shi, Changsha City (CN); Ying Tan, Changsha City (CN); Guangbo Tang, Changsha City (CN); Ning Li, Changsha City (CN)

(73) Assignee: XIANGYA HOSPITAL OF CENTRAL SOUTH UNIVERSITY, Changsha City (CN)

( * ) Notice: Subject to any disclaimer, the term of this patent is extended or adjusted under 35 U.S.C. 154(b) by 0 days.

(21) Appl. No.: 18/925,987

(22) Filed: Oct. 24, 2024

(65) Prior Publication Data

US 2026/0021234 A1     Jan. 22, 2026

(30) Foreign Application Priority Data

Jul. 17, 2024    (CN) .......................... 202410959111.9

(51) Int. Cl.
   *A61M 1/34*       (2006.01)
   *A61M 1/36*       (2006.01)
         (Continued)

(52) U.S. Cl.
   CPC ........ *A61M 1/3451* (2014.02); *A61M 1/3455* (2013.01); *A61M 1/3496* (2013.01);
         (Continued)

(58) Field of Classification Search
   CPC .............. A61M 1/3451; A61M 60/279; A61M 60/113; A61M 1/3455; A61M 1/3496;
         (Continued)

(56) References Cited

U.S. PATENT DOCUMENTS

2023/0402171 A1* 12/2023 Case ...................... A61B 34/10

FOREIGN PATENT DOCUMENTS

CN      113679901 A   * 11/2021  ............. A61M 1/36
CN      118662719 A     9/2024

OTHER PUBLICATIONS

First Office Action issued by The State Intellectual Property Office of People's Republic of China for related application CN202410959111.9, dated Jan. 9, 2025.

* cited by examiner

*Primary Examiner* — Rebecca E Eisenberg
*Assistant Examiner* — Timothy L Flynn
(74) *Attorney, Agent, or Firm* — Thomas | Horstemeyer, LLP

(57) ABSTRACT

An optimizing device for freely switching RBC removal and plasma exchange are provided, which is used to solve the problems in the prior art that the treatment effect is poor, the consumption of consumables is excessive, and the application range is narrow. According to the device, an additional hanging hook is added, a plasma exchange output pipeline is modified to be separated from the plasma collection pump and to be installed to the additional hanging hook. Then, the RBC recirculation tube is clamped through a freely movable cassette, so that the flow rate control of a plasma collection (Continued)

pump is released. Thereafter, HCT data is adjusted, and liquid is compensated, so that the RBC removal or replacement, lymphoplasma exchange and plasma exchange can be freely switched, which can meet the clinical treatment needs, optimize the process and reduce the cost. Therefore, the application range of a pipeline is greatly increased.

8 Claims, 4 Drawing Sheets

(51) Int. Cl.
  *A61M 60/113*   (2021.01)
  *A61M 60/279*   (2021.01)
  *A61M 60/37*   (2021.01)

(52) U.S. Cl.
  CPC ........ *A61M 1/3653* (2013.01); *A61M 1/3672* (2013.01); *A61M 1/3693* (2013.01); *A61M 60/113* (2021.01); *A61M 60/279* (2021.01); *A61M 60/37* (2021.01); *A61M 2202/0415* (2013.01); *A61M 2202/0429* (2013.01); *A61M 2202/0439* (2013.01); *A61M 2205/3331* (2013.01); *A61M 2205/3382* (2013.01); *A61M 2205/3386* (2013.01)

(58) Field of Classification Search
  CPC .............. A61M 1/3653; A61M 1/3672; A61M 1/3693; A61M 2202/0415; A61M 2202/0429; A61M 2202/0439; A61M 2205/3331; A61M 2205/3382; A61M 2205/3386
  See application file for complete search history.

OPTIMIZING DEVICE FOR FREELY SWITCHING BETWEEN BLOOD CELL COMPONENT REMOVAL AND PLASMA EXCHANGE

CROSS-REFERENCE TO RELATED APPLICATION

This patent application claims the benefit and priority of Chinese Patent Application No. 2024109591119 filed with the China National Intellectual Property Administration on Jul. 17, 2024, the disclosure of which is incorporated by reference herein in its entirety as part of the present application.

TECHNICAL FIELD

The present disclosure relates to the technical field of medical instruments, in particular to a device of freely switching and optimizing blood cell component removal and plasma exchange.

BACKGROUND

In recent years, the incidence of complicated and critical diseases has been increasing year by year. Conventional treatment of such diseases is poor in effect, poor in prognosis and high in mortality, which seriously threatens the lives and health of people in China. The pathogenesis of such diseases often involves the immune disorder and imbalance of the body, and it is necessary to rebuild the immune balance of the body by removing immunocompetent cells such as lymphocytes and activated macrophages and related pathogenic antibodies to achieve a stable curative effect. At present, the treatment of immune active cell removal and plasma exchange has become more and more prominent in the treatment of complicated and critical patients clinically. The treatment method of combining the two treatment methods of removing immune active cells such as lymphocytes and plasma exchange is referred to as lymphoplasma exchange. The technology of combining a plurality of treatment technologies such as plasma exchange, red blood cell exchange and leukocyte removal is referred to as whole blood exchange. The whole blood exchange not only can remove the metabolic end products such as destructive antibodies, antigen-antibody complexes, inflammatory mediators and hemoglobin by-products (free iron and methemoglobin) in plasma of a patient, but also remove immunocompetent cells that produce antibodies and red blood cells sensitized by antibodies, alleviate the further damage of hemolytic factors to the tissues and organs of the body. At the same time, the red blood cells exchanged into the body of the patient are more likely to survive in patient, thus quickly alleviating the progress of hemolysis of the patient and providing a better opportunity for clinical treatment. The whole blood exchange is widely used in the treatment of various hemolytic diseases, such as autoimmune hemolytic anemia, mismatched blood transfusion, drug-induced hemolysis and passenger lymphocyte syndrome. The method of combining the whole blood exchange with the lymphoplasma exchange, which can be used flexibly according to the clinical requirements of diseases. These technologies are collectively referred to as therapeutic blood component removal and plasma exchange.

The application of these technologies in the treatment of complicated and critical patients is getting more and more significant. The traditional treatment methods such as red blood cell removal, lymphocyte removal and plasma exchange can only be carried out separately, a plurality of sets of consumables need to be prepared, and different procedures are selected on the same machine in sequence to meet clinical requirements.

First, the curative effect of separate treatment is not exact. Second, it takes a lot of time to replace consumables, which is not conducive to clinical operation and increases the economic burden of patients. The price is very high.

In recent years, many experts and scholars have been trying and improving, aiming at developing the operation mode of therapeutic blood component removal and plasma exchange, which can realize a plurality of treatments in the same set of pipelines. For example, COBE Spectra from Termer and FRESENIUSKABI from Fessenius have realized a plurality of program operations in a set of pipelines through relevant improvements, which greatly meets the clinical treatment requirements. However, with the upgrading of instruments and the redesign of pipelines, in the new generation of Spectra Optia from Termer, the modes such as manual operation are cancelled in instrument design, the pipeline design is more conservative and strict, and the flexibility of adjusting the plasma exchange and cell component removal becomes worse, so that the operations such as free adjustment and switching that could have been realized on the old generation of instruments are unable to meet the clinical treatment requirements because of the design of the instrument program and the pipeline restriction. It is necessary to return to the traditional single program and a plurality of sets of pipelines, which not only increases the treatment cost, but also takes more time, and greatly reduces the curative effect.

Therefore, it is particularly important to realize an optimizing device for freely switching between blood cell component removal and plasma exchange by adjusting the operating procedure of the new Spectra Optia instrument and modifying the pipeline, which is ultimately beneficial to clinical treatment.

SUMMARY

The purpose of the present disclosure is to provide an optimizing device for freely switching between blood cell component removal and plasma exchange, which solves the problems in the prior art that the treatment effect is poor, the consumption of consumables is excessive, the time consumption is long, the cost is high, and the clinical application range of equipment is narrow when red blood cell removal and exchange, lymphocyte removal and plasma exchange are carried out separately in the prior art.

In order to solve the technical problems, the present disclosure uses the following technical scheme.

The present disclosure provides a device of freely switching and optimizing blood cell component removal and plasma exchange, which includes a blood component separator, an external exchange replacement liquid pathway, a waste liquid collection bag, a centrifugal separation belt, a pipeline clamping plate, a saline pipeline, an anticoagulant pipeline, a blood collection pipeline, a recirculation pipeline, an anticoagulation pump, a blood collection pump, a plasma collection pump, a replacement liquid pump, and a blood recirculation pump;

wherein the blood component separator includes a blood cell recirculation pathway and a plasma exchange output pathway;

the blood collection pipeline is provided with a blood collection pipeline sieve tube and a blood collection pressure sensor, and the blood collection pipeline sieve tube and the blood collection pressure sensor are limited on the pipeline clamping plate;

the recirculation pipeline is provided with a blood reservoir and a recirculation pressure sensor, wherein a high liquid level sensor and a low liquid level sensor which are configured to detect a liquid level are provided in the blood reservoir; and a blood reservoir filter is further provided at a bottom of the blood reservoir;

the pipeline clamping plate is provided with a blood cell valve which is configured to adjust a red blood cell delivery pipe; and the pipeline clamping plate is further provided with a red blood cell detector.

Further, an upper end of the external exchange replacement liquid pathway is communicated with a replacement liquid bag, and plasma, red blood cells or other replacement liquid components of a donor are pre-filled in the replacement liquid bag;

wherein the replacement liquid pump is used to convey the plasma, red blood cells or other replacement liquid components of a donor in the replacement liquid bag to the blood reservoir through the external exchange replacement liquid pathway, and is used to be recirculated to the patient together with the cell components in the blood cell recirculation pathway.

Still further, a collection bag scale is provided on the waste liquid collection bag, and a liquid level sensor is provided at a bottom of the waste liquid collection bag;

the plasma exchange output pathway conveys the components to be removed to the waste liquid collection bag through the plasma collection pump, and the waste liquid collection bag is provided on a hanging hook above the blood component separator.

Still further, a pipeline hook is provided on the pipeline clamping plate, and a plasma exchange output pathway is hung on the pipeline hook.

Still further, the blood component separator is connected with the blood collection pathway, a blood separation pathway and the blood recirculation pathway through pipelines;

wherein one end of the blood collection pathway is used to collect blood; the blood separation pathway is connected with the blood cell recirculation pathway and the plasma exchange output pathway, wherein the plasma exchange output pathway is communicated with the waste liquid collection bag; and the blood recirculation pathway is connected with the blood cell recirculation pathway and the external exchange replacement liquid pathway, and is connected with a vein of a patient through a recirculation end of the blood component separator.

Still further, the plasma collection pump transports the components to be removed to the waste liquid collection bag;

the replacement liquid pump conveys the plasma, red blood cells or other replacement liquid components of a donor in the replacement liquid bag to the blood reservoir;

the blood collection pathway and the blood component separator are connected with the anticoagulant pathway, and an upper end of the anticoagulant pathway is communicated with an anticoagulant bag; wherein the anticoagulant pathway transports the anticoagulant in the anticoagulant pathway into the blood collection pathway through the anticoagulation pump to be mixed with blood.

Still further, the blood recirculation pathway is connected with the blood cell recirculation pathway and the external exchange replacement liquid pathway through the blood reservoir;

a freely movable cassette (an additional manually controlled hemostatic forceps clamp) is provided on the blood cell recirculation pathway, which is configured to clamp the blood cell recirculation pathway;

the freely movable cassette is an additional manually controlled hemostatic forceps clamp, and the blood cell recirculation pathway is clamped shut by the manually controlled hemostatic forceps clamp.

Still further, a plasma valve which is configured to adjust the plasma exchange output pathway is provided on the pipeline clamping plate; and the pipeline clamping plate is further provided with a removal valve which is configured to adjust the opening and closing of the external exchange replacement liquid pathway.

Compared with the prior art, the present disclosure has the following beneficial technical effects.

The optimizing device for freely switching between blood cell component removal and plasma exchange according to the present disclosure improves the free clamping and the pipeline installation of the blood cell recirculation pipeline on the basis of plasma exchange, and releases the flow rate control of the plasma collection pump by adding an additional hanging hook and a liquid level sensor.

A volume scale is marked on a waste liquid collection bag. Thereafter, HCT data of a patient is adjusted, and liquid is compensated, so that the treatment operations such as red blood cell removal or replacement, lymphocyte removal and plasma exchange can be freely switched or carried out at the same time on a Spectra Optia blood component separator using the same consumable pipeline, which can meet the clinical treatment purpose to the greatest extent, improve the treatment effect, optimize the treatment process and reduce the treatment cost.

Therefore, not only the clinical application range of an instrument pipeline is greatly increased, but also the treatment requirements can be freely switched and selected.

BRIEF DESCRIPTION OF THE DRAWINGS

The present disclosure will be further described with reference to the accompanying drawings hereinafter.

DESCRIPTION OF REFERENCE NUMERALS

Figure 1:
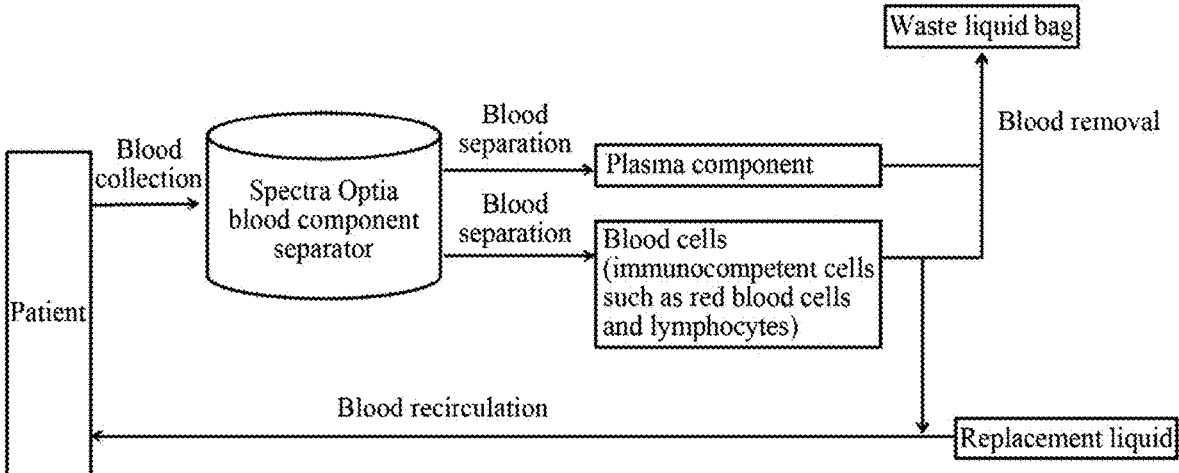
FIG. 1 is a schematic flow diagram of a system of a device of freely switching and optimizing blood cell component removal and plasma exchange according to the present disclosure.
Figure 2:
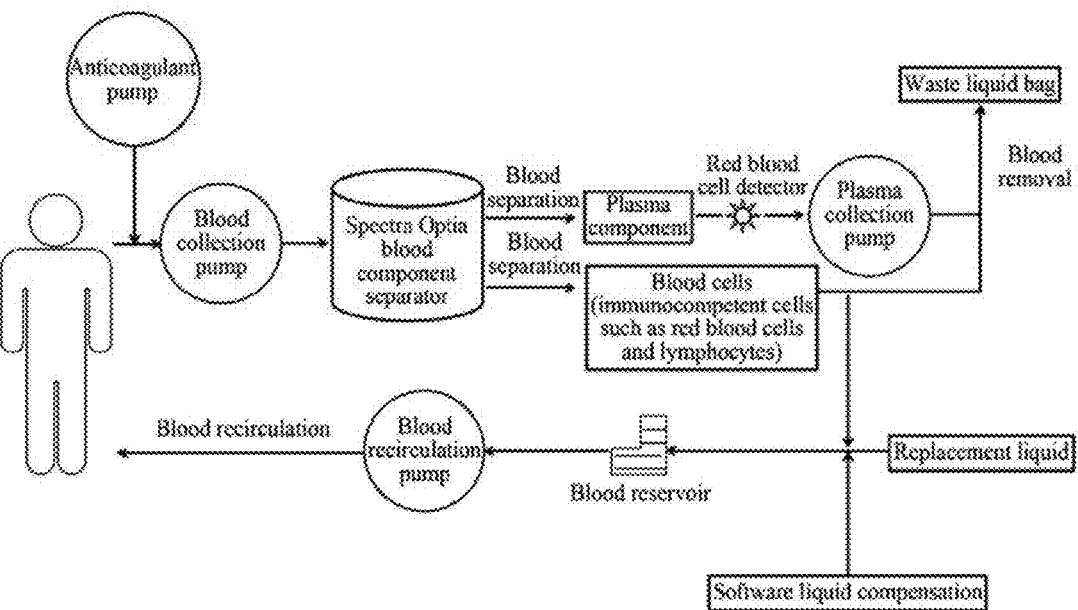
FIG. 2 is a schematic diagram of an operation structure of a device of freely switching and optimizing blood cell component removal and plasma exchange according to the present disclosure.
Figure 3:
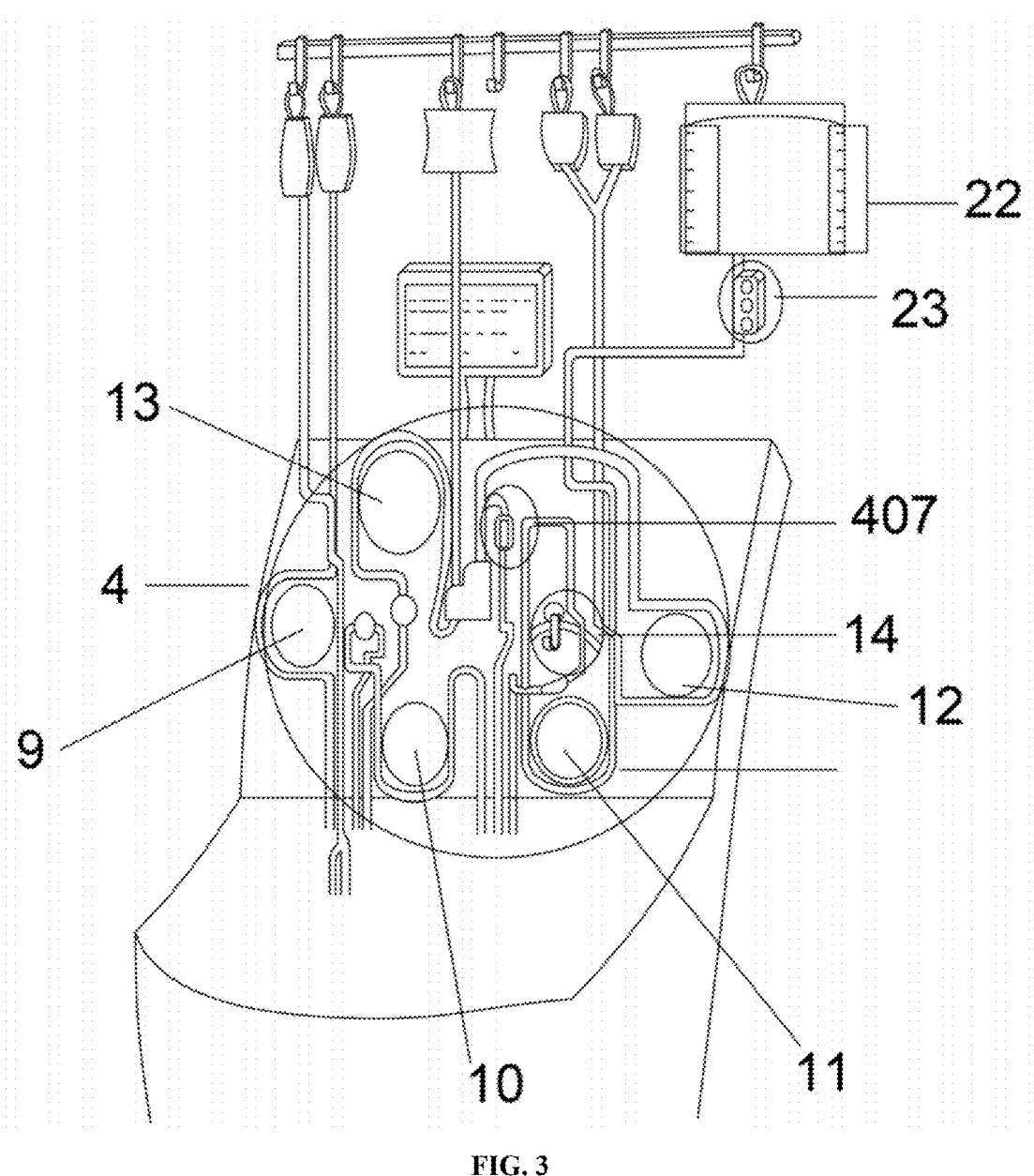
FIG. 3 is a perspective view of a device of freely switching and optimizing blood cell component removal and plasma exchange according to the present disclosure.
Figure 4:
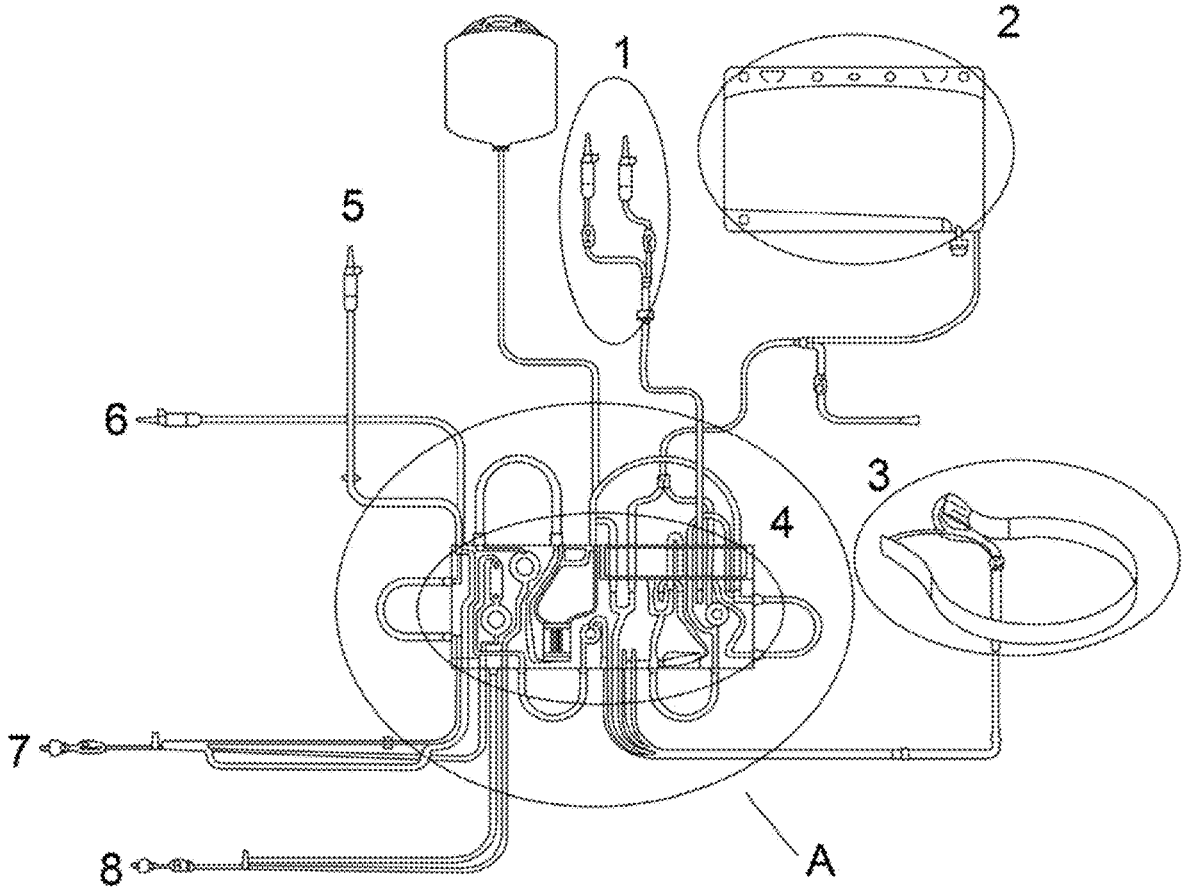
FIG. 4 is a schematic structural diagram of a pipeline assembly of a device of freely switching and optimizing blood cell component removal and plasma exchange according to the present disclosure.
Figure 5:
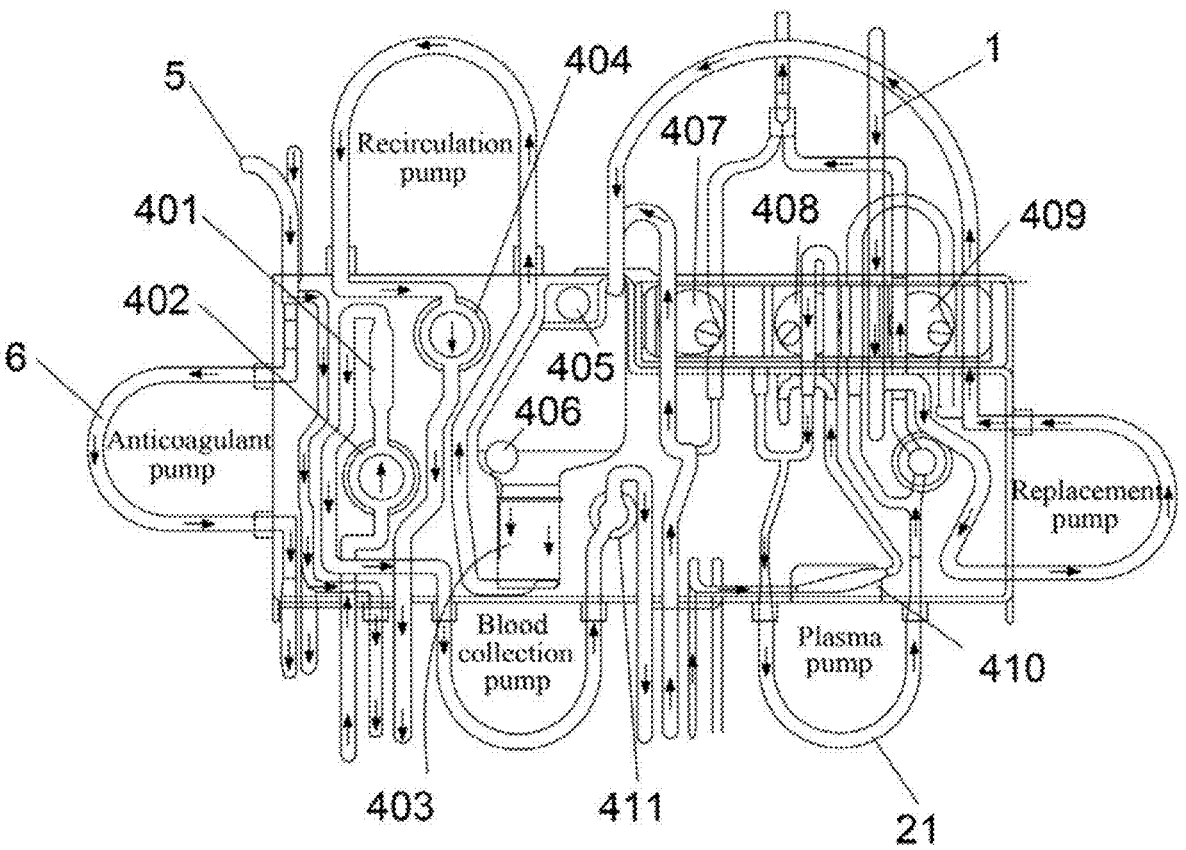
FIG. 5 is an enlarged view of part A in FIG. 4.

1. External exchange replacement liquid pathway; 2. Waste liquid collection bag; 21. Plasma exchange output pathway; 22. Collection bag scale; 23. Liquid level sensor;

3. Centrifugal separation belt; 4. Pipeline clamping plate; 401. Blood collection pipeline sieve tube; 402. Blood collection pressure sensor; 403. Blood reservoir filter; 404. Recirculation pressure sensor; 405. High liquid level sensor; 406. Low liquid level sensor; 407. Blood cell valve; 408. Plasma valve; 409. Removal valve; 410. Red blood cell detector; 411. Centrifugal pressure sensor; 5. Saline pipeline; 6. Anticoagulant pipeline; 7. Blood collection pipeline; 8. Recirculation pipeline; 9. Anticoagulation pump; 10. Blood collection pump; 11. Plasma collection pump; 12. Replacement liquid pump; 13. Blood recirculation pump; 14. Pipeline hook.

DETAILED DESCRIPTION OF THE EMBODIMENTS

In this embodiment, a device of freely switching and optimizing blood cell component removal and plasma exchange is disclosed, which includes a blood component separator, an external exchange replacement liquid pathway 1, a waste liquid collection bag 2, a centrifugal separation belt 3, a pipeline clamping plate 4, a saline pipeline 5, an anticoagulant pipeline 6, a blood collection pipeline 7, a recirculation pipeline 8, an anticoagulation pump 9, a blood collection pump 10, a plasma collection pump 11, a replacement liquid pump 12, and a blood recirculation pump 13.

The blood component separator needs to be equipped with a disposable blood cell separator (a pipeline with the model 10226), and the blood component separator is connected with the blood collection pathway 7, a blood separation pathway and the blood recirculation pathway 8 through pipelines.

In this embodiment, the blood component separator is a Spectra Optia blood component separator; wherein the blood collection pathway 7 is connected with the median cubital vein, the radial artery or the arteria dorsalis pedis of a patient for collecting blood. The blood separation pathway is connected with the blood cell recirculation pathway and the plasma exchange output pathway 21, wherein the plasma exchange output pathway 21 is communicated with the waste liquid collection bag 2; and the blood recirculation pathway 8 is connected with the blood cell recirculation pathway and the external exchange replacement liquid pathway 1, and is connected with a vein of a patient through a recirculation end of the blood component separator.

In the above implementing process, the blood collection pump 10 transports blood in the body of the patient to the Spectra Optia blood component separator through collection blood vessels such as the median cubital vein, the radial artery or the arteria dorsalis pedis via the blood collection pathway 7. The Spectra Optia blood component separator separates the collected blood from the patient into cell components and plasma components in blood by centrifugation, wherein the cell components include tangible components such as red blood cells, white blood cells and platelets; and white blood cells include immunocompetent cells such as neutrophils and lymphocytes.

The separated blood components are transported to the blood cell recirculation pathway and the plasma exchange output pathway through the blood separation pathway of the blood component separator, respectively. The plasma collection pump 11 transports the components to be removed to the waste liquid collection bag 2.

The replacement liquid pump 12 conveys the plasma, red blood cells or other replacement liquid components of a donor in the replacement liquid bag to the blood reservoir, so as to be recirculated to the patient together with the cell components in the blood cell recirculation pathway. The pipelines are communicated through instruments.

In a specific embodiment, the blood collection pathway 7 and the Spectra Optia blood component separator are connected with the anticoagulant pathway 6, and the upper end of the anticoagulant pathway 6 is communicated with an anticoagulant bag. The anticoagulant bag is hung above the Spectra Optia blood component separator; wherein the anticoagulant pathway 6 transports the anticoagulant in the anticoagulant pathway into the blood collection pathway 7 through the anticoagulation pump 9 to be mixed with blood for preventing blood coagulation. The collected blood mixed with the anticoagulant enters the blood separation belt 3 via the collection pathway through the blood collection pump 10 for separation.

In the above implementation, the collected blood enters the blood separation pathway after being separated by the blood separation belt 3, and the blood separation pathway is connected with the blood cell recirculation pathway and the plasma exchange output pathway, respectively.

In the above specific embodiment, the plasma exchange output pathway in the Spectra Optia blood component separator conveys the components to be removed (immunocompetent cells such as plasma, neutrophils and lymphocytes and components other than red blood cells) to the waste liquid collection bag 2 through the plasma collection pump 11. The waste liquid collection bag 2 is installed on the hanging hook above the Spectra Optia blood component separator.

In a specific embodiment, the venous recirculation of the patient is connected with the blood recirculation pathway 8, and the blood recirculation pathway 8 is connected with the blood cell recirculation pathway (mainly conveying red blood cells) and the external exchange replacement liquid path 1 through the blood reservoir.

In the implementing process, it is necessary to add a freely movable cassette (specifically, an additional manually controlled hemostatic forceps clamp) to the blood cell recirculation pathway at the upper end of the blood reservoir, which is configured to clamp the pathway. It is controlled whether the components in the blood cell recirculation pathway enter the blood reservoir by opening the pathway, so as to control the components to enter the body of the patient.

In the above embodiment, after the blood cell recirculation pathway is clamped by the freely movable cassette (an additional manually controlled hemostatic forceps clamp), the blood cell components cannot be pumped out of the blood separation pathway due to the control and restriction of the flow rate of the plasma collection pump 11, so that a large number of cell components are stored in the blood separation belt 3, and the centrifugal pressure alarm is triggered.

In the above specific implementation, first, the red blood cell detector 410 on the plasma exchange output pathway is deactivated. The plasma exchange output pathway 21 is separated from the plasma collection pump 11, so that the flow rate limit of automatic recognition of plasma collection is artificially released, thereby preventing the centrifugal pressure alarm induced by the storage of a large number of cells. At the same time, a hanging hook is added above the installing panel to flexibly fix the plasma exchange output pathway at the plasma collection pump 11, and prevent the plasma exchange pathway from rotating into the plasma collection pump 11. In addition, an external liquid level sensor 23 is installed on the plasma exchange output pathway 21 to sense the normal flow of liquid.

The present disclosure provides a method of installing a 10226 pipeline on a new generation of Spectra Optia instruments from Terumo. First, the red blood cell recirculation tube is clamped through a freely movable cassette (additional manually controlled hemostatic forceps clamp) to seal the red blood cell recirculation pathway of the patient.

Second, the plasma exchange output pipeline is modified to be separated from the plasma collection pump 11 and to be installed to an additional pipeline hook 14 above the panel, so as to remove the flow rate restriction of the plasma collection pump 11 on the blood component removal. At the same time, an external liquid level sensor 23 is installed on the plasma exchange output pipeline.

Third, the liquid balance is achieved by adjusting the HCT data of the patient and the liquid compensation mode. Finally, the collection bag scale 22 of the collection volume is marked on the waste liquid collection bag 2 of blood components, so as to observe whether the data of input and output liquid is balanced.

Therefore, the new Spectra Optia instrument can realize the mode of freely switching and optimizing blood cell component removal and plasma exchange, and achieve the clinical treatment purpose that the treatment operations such as red blood cell removal or exchange, lymphocyte removal and plasma exchange can be switched freely or carried out simultaneously, so as to improve the treatment effect, optimize the treatment process and reduce the treatment cost.

The above embodiment only describes the preferred mode of the present disclosure, rather than limit the scope of the present disclosure. Based on the premise of not departing from the design spirit of the present disclosure, various modifications and improvements made to the technical scheme of the present disclosure by those skilled in the art shall fall within the scope of protection determined by the claims of the present disclosure.

What is claimed is:

1. An optimizing device for freely switching between blood cell component removal and plasma exchange, which comprises a blood component separator, an external exchange replacement liquid pathway (1), a waste liquid collection bag (2), a centrifugal separation belt (3), a pipeline clamping plate (4), a saline pipeline (5), an anticoagulant pipeline (6), a blood collection pipeline (7), a recirculation pipeline (8), an anticoagulation pump (9), a blood collection pump (10), a plasma collection pump (11), a replacement liquid pump (12), and a blood recirculation pump (13);

wherein the blood component separator comprises a blood cell recirculation pathway and a plasma exchange output pathway (21);

wherein:

the blood collection pipeline (7) is provided with a blood collection pipeline sieve tube (401) and a blood collection pressure sensor (402), and the blood collection pipeline sieve tube (401) and the blood collection pressure sensor (402) are limited on the pipeline clamping plate (4);

the recirculation pipeline (8) is provided with a blood reservoir and a recirculation pressure sensor (404), wherein a high liquid level sensor (405) and a low liquid level sensor (406) which are configured to detect a liquid level are provided in the blood reservoir; and a blood reservoir filter (403) is further provided at a bottom of the blood reservoir;

the pipeline clamping plate (4) is provided with a blood cell valve (407) which is configured to adjust a red blood cell delivery pipe; and the pipeline clamping plate (4) is further provided with a red blood cell detector (410);

wherein a collection bag scale (22) is provided on the waste liquid collection bag (2), and a liquid level sensor (23) is provided at a bottom of the waste liquid collection bag (2);

a pipeline hook (14) is provided on the pipeline clamping plate (4);

a freely movable cassette is provided on the blood cell recirculation pathway, which is configured to clamp shut the blood cell recirculation pathway;

when implementing, first, deactivating the red blood cell detector (410) on the plasma exchange output pathway, separating the plasma exchange output pathway (21) from the plasma collection pump (11), so that the flow rate limit of automatic recognition of plasma collection is artificially released, thereby preventing the centrifugal pressure alarm induced by the storage of a large number of cells, at the same time, adding a hanging hook above the installing panel to flexibly fix the plasma exchange output pathway at the plasma collection pump (11), and preventing the plasma exchange pathway from rotating into the plasma collection pump (11), further, installing an external liquid level sensor (23) on the plasma exchange output pathway (21) to sense the normal flow of liquid.

2. The optimizing device for freely switching between blood cell component removal and plasma exchange according to claim 1, wherein an upper end of the external exchange replacement liquid pathway (1) is communicated with a replacement liquid bag, and plasma, red blood cells or other replacement liquid components of a donor are pre-filled in the replacement liquid bag;

wherein the replacement liquid pump (12) is used to convey the plasma, red blood cells or other replacement liquid components of a donor in the replacement liquid bag to the blood reservoir through the external exchange replacement liquid pathway (1), and is used to be recirculated to the patient together with the cell components in the blood cell recirculation pathway.

3. The optimizing device for freely switching between blood cell component removal and plasma exchange according to claim 1, wherein the plasma exchange output pathway (21) conveys the components to be removed to the waste liquid collection bag (2) through the plasma collection pump (11), and the waste liquid collection bag (2) is provided on a hanging hook above the blood component separator.

4. The optimizing device for freely switching between blood cell component removal and plasma exchange according to claim 1, wherein a plasma exchange output pathway is hung on the pipeline hook (14).

5. The optimizing device for freely switching between blood cell component removal and plasma exchange according to claim 1, wherein the blood component separator is connected with the blood collection pipeline (7), a blood separation pathway and the recirculation pipeline (8) through pipelines;

wherein one end of the blood collection pipeline (7) is used to collect blood; the blood separation pathway is connected with the blood cell recirculation pathway and the plasma exchange output pathway (21), wherein the plasma exchange output pathway (21) is communicated with the waste liquid collection bag (2); and the recirculation pipeline (8) is connected with the blood cell recirculation pathway and the external exchange replacement liquid pathway (1), and is connected with a vein of a patient through a recirculation end of the blood component separator.

6. The optimizing device for freely switching between blood cell component removal and plasma exchange according to claim 5, wherein the plasma collection pump (11) transports the components to be removed to the waste liquid collection bag (2);

the replacement liquid pump (12) conveys the plasma, red blood cells or other replacement liquid components of a donor in the replacement liquid bag to the blood reservoir;

the blood collection pipeline (7) and the blood component separator are connected with the anticoagulant pipeline (6), and an upper end of the anticoagulant pipeline (6) is communicated with an anticoagulant bag; wherein the anticoagulant pipeline (6) transports the anticoagulant in the anticoagulant pathway into the blood collection pipeline (7) through the anticoagulation pump (9) to be mixed with blood.

7. The optimizing device for freely switching between blood cell component removal and plasma exchange according to claim 1, wherein the recirculation pipeline (8) is connected with the blood cell recirculation pathway and the external exchange replacement liquid pathway (1) through the blood reservoir;

the freely movable cassette is an additional manually controlled hemostatic forceps clamp, and the blood cell recirculation pathway is clamped shut by the manually controlled hemostatic forceps clamp.

8. The optimizing device for freely switching between blood cell component removal and plasma exchange according to claim 1, wherein a plasma valve (408) which is configured to adjust the plasma exchange output pathway (21) is provided on the pipeline clamping plate (4); and the pipeline clamping plate (4) is further provided with a removal valve (409) which is configured to adjust the opening and closing of the external exchange replacement liquid pathway (1).

* * * * *